United States Patent
Tanki et al.

(10) Patent No.: US 8,104,389 B2
(45) Date of Patent: Jan. 31, 2012

(54) VIBRATING MICROTOME WITH AUTOMATED MEASUREMENT OF VERTICAL RUNOUT

(75) Inventors: Siegfried Tanki, Vienna (AT); Felix Redl, Vienna (AT)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 13/094,906

(22) Filed: Apr. 27, 2011

(65) Prior Publication Data

US 2011/0197731 A1 Aug. 18, 2011

Related U.S. Application Data

(63) Continuation of application No. 11/847,861, filed on Aug. 30, 2007, now Pat. No. 7,954,406.

(30) Foreign Application Priority Data

Sep. 2, 2006 (DE) .......................... 10 2006 041 208

(51) Int. Cl.
  *B26D 1/00* (2006.01)
(52) U.S. Cl. ......................................... 83/651; 83/915.5
(58) Field of Classification Search ................... 83/76.1, 83/76.6–76.7, 746, 748, 915.5, 651
  See application file for complete search history.

(56) References Cited

U.S. PATENT DOCUMENTS

| | | | |
|---|---|---|---|
| 3,688,500 A | 9/1972 | Chancel | |
| 4,239,963 A * | 12/1980 | August et al. | 73/514.26 |
| 4,377,958 A | 3/1983 | Leighton | |
| 4,566,225 A | 1/1986 | Bizot et al. | |
| 4,731,733 A | 3/1988 | Knoll | |
| 4,966,460 A * | 10/1990 | Kahley | 356/640 |
| 5,043,907 A | 8/1991 | Richards | |
| 5,067,379 A | 11/1991 | Butler et al. | |
| 5,226,335 A | 7/1993 | Sitte et al. | |
| 5,461,953 A | 10/1995 | McCormick | |
| 5,850,772 A | 12/1998 | Hayashi | |
| 5,860,349 A | 1/1999 | Takeda | |
| 5,906,148 A | 5/1999 | Aihara et al. | |
| 5,985,217 A | 11/1999 | Krulevitch et al. | |
| 5,995,230 A * | 11/1999 | Madlener et al. | 356/614 |
| 6,041,686 A | 3/2000 | Lihl et al. | |

(Continued)

FOREIGN PATENT DOCUMENTS

DE  202004007658 U1  7/2004

(Continued)

OTHER PUBLICATIONS

Geiger et al.; Patch-clamp recording in brain slices with improved slicer technology; Pfluegers Arch—European Journal of Physiology, 2002, vol. 443; pp. 491-501; published online Oct. 17, 2001.

*Primary Examiner* — Sean Michalski
(74) *Attorney, Agent, or Firm* — Hodgson Russ LLP

(57) ABSTRACT

A vibrating microtome and measuring device for measuring the transverse offset of a vibrating knife comprises a light barrier into which the knife is placeable and a control application signal (pklo, pkhi) that describes the time course of the vibration of the knife and an electronic measurement system of the measuring device measures the coverage of the light barrier as an oscillating signal (tpm), and determines the transverse offset from the signal values at points in time that are defined by the control application signal.

8 Claims, 3 Drawing Sheets

U.S. PATENT DOCUMENTS

| | | |
|---|---|---|
| 6,105,483 A | 8/2000 | Takeda |
| 6,330,348 B1 | 12/2001 | Kerschmann et al. |
| 6,628,408 B1 | 9/2003 | Franklin et al. |
| 6,869,006 B2 | 3/2005 | Franklin et al. |
| 7,954,406 B2 | 6/2011 | Tanki et al. |
| 2002/0020266 A1 | 2/2002 | Smith |
| 2006/0119908 A1 | 6/2006 | Harris et al. |
| 2007/0095188 A1 | 5/2007 | Lang et al. |
| 2007/0177162 A1 | 8/2007 | Glueck |
| 2008/0072722 A1 | 3/2008 | Tanki et al. |
| 2008/0094640 A1 | 4/2008 | Cordingley et al. |
| 2008/0278099 A1 | 11/2008 | Bergfors et al. |

FOREIGN PATENT DOCUMENTS

| | | |
|---|---|---|
| JP | 10296588 A | 11/1998 |

* cited by examiner

VIBRATING MICROTOME WITH AUTOMATED MEASUREMENT OF VERTICAL RUNOUT

CROSS REFERENCE TO RELATED APPLICATIONS

This application claims priority of German patent application 10 2006 041 208.7 filed Sep. 2, 2006, which is incorporated by reference herein.

FIELD OF THE INVENTION

The present invention relates to a device for measuring the vertical runout in a vibrating microtome. More precisely, the invention relates to a vibrating microtome in which a knife is configured, in particular during a sectioning operation, to vibrate in a direction parallel to a section plane and substantially (i.e. within alignment accuracy values) parallel to a cutting edge of the knife, and to a pertinent measuring device that, for measurement of the transverse offset of the cutting edge in the context of its lateral vibratory motion as a consequence of a potentially present inclination of the cutting edge with respect to the section plane, comprises a light barrier into which the cutting edge is placeable, the light barrier being oriented in a direction parallel to the section plane and the cutting edge partially covering the light beam of the light barrier; the fluctuation over time of the measured signal derived from the light barrier, which fluctuation is occurring because of the vibration of the knife, is used to determine the transverse offset.

BACKGROUND OF THE INVENTION

Vibrating microtomes in which the cutting edge performs an oscillating horizontal motion along the direction of the cutting edge, while the material being sectioned advances in the other horizontal direction and is thus sectioned along a horizontal sectioning surface, are well known, for example from the Applicant's DE 196 45 107 C2 and DE 20 2004 007 658 U1. Vibrating microtomes of this kind are used in particular to section tissue specimens in liquids (buffer solutions), for example brain tissue, or other materials of low plastic stability and/or gel-like consistency. In one usual geometry, the sample is fed forward vertically (Z axis) and stepwise from bottom to top. During an individual sectioning operation, the knife moves at the sectioning speed horizontally (X axis) with respect to the sample. In that context, it vibrates substantially parallel to the cutting edge in a vibration direction that is perpendicular (Y axis) to the other motion directions, the vibration frequency being typically on the order of 100 Hz, for example in the range from 90 to 100 Hz. Because of the tolerances of the knife holder and knife, however, it is inevitable that the knife edge does not move exactly parallel to the vibration direction. A knife that is clamped in obliquely produces, because of the vibration, a corresponding motion in the Z direction; this transverse vibratory offset (i.e. perpendicular to the section plane, thus extending in the Z direction in this case) is also referred to as vertical runout. The consequence of a vertical runout is that the sections exhibit a wave-like pattern.

An electrical control system of a vibrating microtome is described in the article "Patch-clamp recording in brain slices with improved slicer technology," Pflügers Arch—Eur. J. Physiol. (2002) 443:491-501 by J. R. P. Geiger et al., who propose a measuring head (referred to as a "vibroprobe") as an aid to determining the transverse offset occurring in the context of knife oscillation. The measuring head operates with an IR light beam that is emitted by an LED and detected in a photodiode, and measures the magnitude, or the change over time in said magnitude, of the (partial) coverage of the light beam by the cutting edge positioned in the beam path. The vertical runout occurring as a consequence of the oscillating motion of the cutting edge thus yields an oscillating output signal whose vibration amplitude is to be minimized by appropriate manual adjustment of the alignment of the cutting edge. By means of a setting screw (for tilting the knife), the knife edge is aligned parallel to the vibration direction and the vertical runout of the knife is thus reduced to a minimum. This operation of aligning the knife edge is time-consuming and cumbersome, not least because pivoting of the knife is generally associated with a realignment of the Z position. A rapid alignment operation, on the other hand, is of great advantage, given that the samples are short-lived and must be processed quickly.

SUMMARY OF THE INVENTION

It is therefore an object of the invention to indicate a way to simplify and speed up alignment of the knife in terms of vertical runout, and to configure said alignment reliably for the entire range of possible vibration amplitudes and frequencies of the knife.

This object is achieved by an electronic measurement system, provided on a measuring device of the kind described initially, that according to the present invention is configured to accept at least one control application signal that describes the time course of the vibration of the knife, and to perform the determination of the transverse offset of the cutting edge based on the values of the measured signal derived from the light barrier at points in time which are determined from said control application signal. The control application signal is preferably generated on the part of the vibrating microtome on the basis of one or more signal(s) derived from the motion of the knife or of the knife holder.

As a result of this manner according to the present invention of achieving the object, which provides for the use of a constant-phase signal to define the measurement points in time, the accuracy and repeatability of the measurement of the transverse offset (vertical runout) can be substantially increased. It is furthermore easier, or indeed possible at all, to eliminate interfering influences.

A preferred embodiment that additionally simplifies the measurement operation provides for the at least one control application signal to define the position in time of the vibration maxima of the knife, and for the electronic measurement system to derive, from the measured signal, values that correspond to the transverse positions of the cutting edge at times of opposite vibration maxima, and to determine the transverse offset from the difference between those values.

The measuring device can preferably be embodied as a unit detachable from the vibrating microtome, the electronic measurement system being housed in the measuring device. This simplifies operation as well as the accessibility of the sample during the sectioning operation.

The measuring device, especially when it is realized as a detachable unit, can favorably generate a signal that describes the magnitude of the measured transverse offset, and convey said signal to the vibrating microtome so that it can be displayed, for example, on a display associated with the vibrating microtome.

It is additionally useful if the light barrier lies in a direction parallel to the (in this case merely prospective) section plane.

It is furthermore advantageous, in order to preclude interfering influences, if the electronic measurement system is additionally configured to adjust the intensity of the light beam of the light barrier prior to a determination of the transverse offset, namely with the cutting edge in a position completely outside the light barrier, wherein a utilization exceeding 90%, e.g. 95%, of the modulation range of the detector element of the light barrier is established.

In corresponding fashion, the stated object is achieved by a vibrating microtome of the kind cited initially having an electronic control system which is configured to generate, from a vibration signal derived from the vibratory motion of the knife, at least one control application signal that describes the time course of the vibration of the knife; and is furthermore configured, for the purpose of a measurement of the transverse offset of the cutting edge in the context of its lateral vibratory motion due to a potentially present inclination of the cutting edge with respect to the section plane, to deliver said control application signal to a measuring device that is provided on the vibrating microtome and has a light barrier into which the cutting edge is placeable.

Advantageous refinements of the vibrating microtome correspond, mutatis mutandis, to the refinements of the measuring device that are discussed above.

BRIEF DESCRIPTION OF THE DRAWINGS

The invention, together with further advantages, is further explained below with reference to a non-limiting exemplifying embodiment that is depicted in the attached drawings, in which.

DETAILED DESCRIPTION OF THE INVENTION

The exemplifying embodiment presented below relates to a vibrating microtome in which a vertical runout measuring device in the form of a measuring head is installed instead of the sample holder. A determination of the linear modulation range of the detector element is carried out on the part of the measuring head, in the lowered position, at the beginning of each measurement, and the intensity of the light barrier of the transmitting element is set in such a way that the (uncovered) detector element is operated close to the upper limit of its linear modulation range. The measurement itself is performed in the middle of the linear modulation range, typically at 50% occlusion by the knife. The result of this operation is that each measurement operation is individually calibrated and remains largely independent of long-term interfering influences (temperature, extraneous light, component drift).

The measuring head as a whole does not require any adjusting element that would need to be manually equalized. According to the invention, for the measurement operation the measuring device is supplied, by the electronic system of the microtome, with a signal that describes the vibration operation of the knife over time, i.e. defines the exact locations in time of the maximum left and right extension of the vibrating knife. The basis for this control application signal is constituted by a digital measurement of the period of the knife vibration, with the aid of a measurement of the zero crossings of the fed-back knife position signal of the vibratory drive. This guarantees that the resolution of the time measurement is to a very large extent independent of the amplitude and frequency of the vibration. The control application signal comprises signal pulses respectively one-quarter period before and after a zero crossing. Sampling of the actual value of the vibration amplitude is likewise accomplished by means of these signal pulses. This ensures that the determination of the knife obliquity is always performed synchronously with the knife vibration. Because the point in time of the measurement is highly precise, the measurement result is stable over a small fluctuation range and can therefore be determined very accurately: resolutions in the order of magnitude of 0.1% or less have been achieved.

Construction

Figure 1:
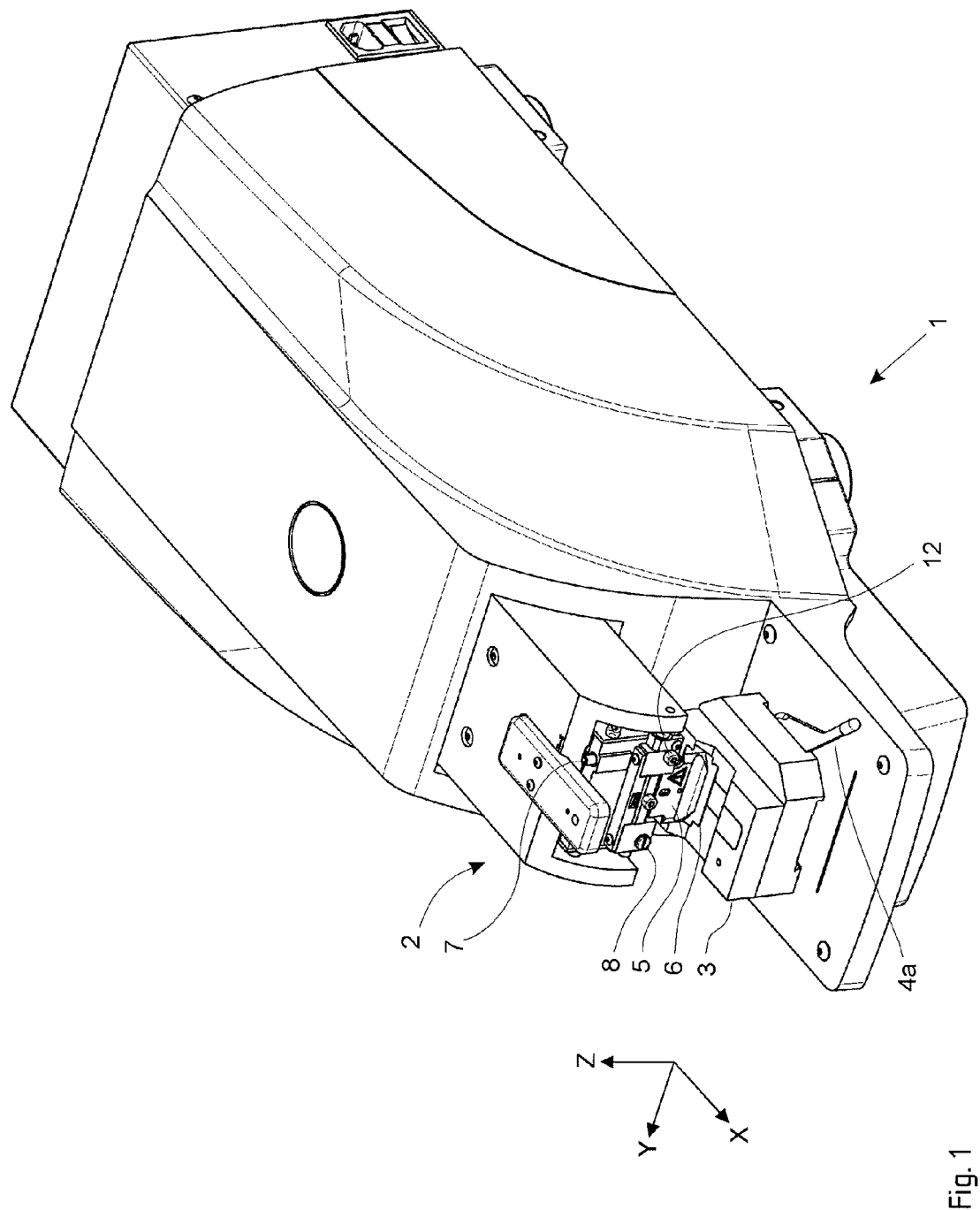
FIG. 1 is a perspective view of a vibrating microtome having a vertical runout measuring head installed.
Figure 2:
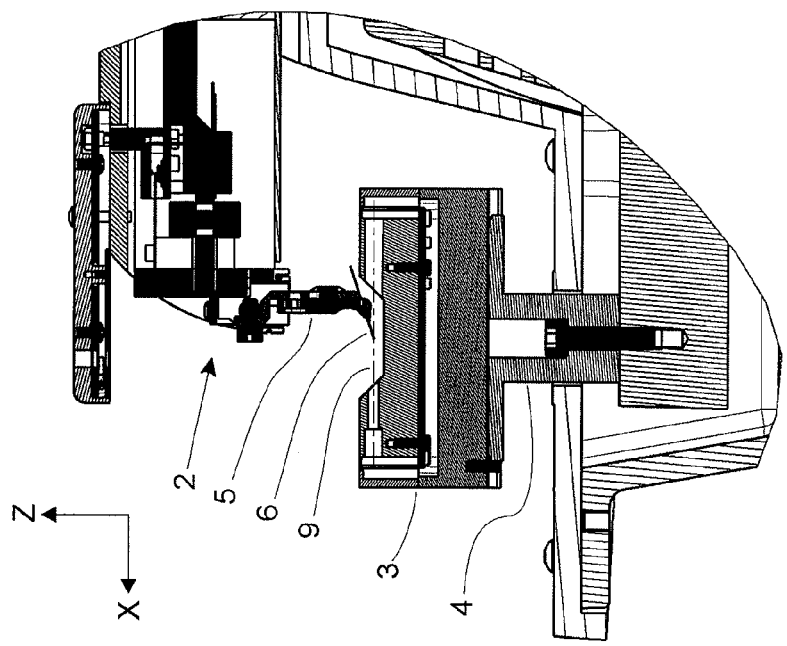
FIG. 2 is a sectioned view through the measuring head and the vibrating head along the vertical center plane of the vibrating microtome of FIG. 1.

FIG. 1 shows a vibrating microtome 1 that is based on the vibrating microtome of J. R. P. Geiger et al. in terms of its external layout and mechanical principle, but whose electronic control system is improved in accordance with the invention, as will be explained below with reference to FIG. 3. Vibrating microtome 1 comprises, in a manner known per se, a vibrating head 2 that, as also shown in FIG. 2, is positioned in the form of an extension arm over the material to be sectioned (sample and sample carrier, not shown) together with its holder 4; in order to measure and compensate for the vertical runout, in place of the sample holder a vertical runout measuring head 3 is installed on holder 4 by means of a clamping mechanism actuable via a clamping lever 4a.

Vibrating head 2 comprises a knife holder 5 in which a knife 6 is held in fixedly clamped fashion. In the exemplifying embodiment depicted, the section plane extends horizontally, and sections that may optionally follow one another proceed vertically one above another. For this purpose, vibrating head 2 and holder 4 (together with measuring head 3) can be moved vertically (Z axis) with respect to one another; the holder comprises for this purpose, for example, a stepping motor (not shown) in the lower region of vibrating microtome 1. By means of a permanent magnet+coil+spring arrangement (not shown; cf in this regard the article by J. R. P. Geiger et al.) housed in vibrating head 2, a vibratory motion proceeding in a horizontal-lateral direction (Y axis) is imparted to knife holder 5 together with knife 6. Vibrating head 2 can be displaced in the horizontal longitudinal direction (X axis) by means of a DC motor (not shown); in addition, a DC motor can likewise be provided in the sample carrier (not shown), which motor serves for a controllable, uniform motion of the sample in the X direction during the sectioning operation while the vibrating head remains stationary in the X direction.

It is not excluded that the three aforesaid directions X, Y, Z can, if necessary, also be oriented differently in other embodiments than in the exemplifying embodiment shown; as is immediately apparent, the terms "horizontal-longitudinal," "horizontal-lateral," and "vertical" that are used here are then to be understood mutatis mutandis, depending on the actual orientation of the X axis (advance direction), Y axis (vibration direction), and Z axis (transverse direction perpendicular to the section plane).

Returning to FIG. 1, knife holder 5 is attached to the front side of vibrating head 2, knife 6 being retained at the lower end and a cutting edge of the knife projecting out of the knife holder. In known fashion, knife 6 is inclined toward the section plane (more precisely, toward the X axis) in order to obtain a desired sectioning result. The cutting edge ideally extends exactly parallel to the Y axis, i.e. perpendicular to the X and Z axes. With the aid of an adjusting screw 7, knife holder 5 can be pivoted about guidance axis 8. One complete rotation of the adjusting screw corresponds, for example, to a 5.3-mrad tilt of the knife (equal to a 5.3-μm change in the vertical runout with reference to a 1-mm horizontal-lateral displacement of the cutting edge).

Referring to FIG. 2, measuring head 3 comprises a light barrier in the X direction that is implemented by means of an IR LED as transmitting element and an IR photodiode as detector. Optical axis 9 of the light barrier is shown in FIG. 2 as a dashed line. The lateral extension of the light barrier (as defined by the lateral extension of the LED and photodiode plus any opening apertures present in the measuring head) is in the order of magnitude of 1 mm, and thus substantially greater than the vertical offset over one vibration amplitude. The knife is positioned so that approximately 50% of the IR light is covered; the photodiode measures the quantity of IR light propagating unimpededly beneath the cutting edge, and thus the amount by which the light barrier is covered by the cutting edge (the knife). The purpose of compensating for vertical runout is to set the path of the cutting edge so that when vibration (oscillation along the Y axis) is switched on, the amount of coverage changes as little as possible over one vibration period—and ideally remains constant.

A limitation of light beam 9 in terms of its extension—in particular in the Z direction, which might represent an alternative approach to enabling a more direct resolution of the Z position of the cutting edge—was not considered because of the drastic loss of light intensity (and therefore sensitivity) associated therewith.

As already mentioned, FIGS. 1 and 2 show vibrating microtome 1 with a measuring head installed for compensating for vertical runout. After knife holder 5 is adjusted, the measuring head is removed and is replaced with the sample carrier having the sample that is to be sectioned.

Figure 3:
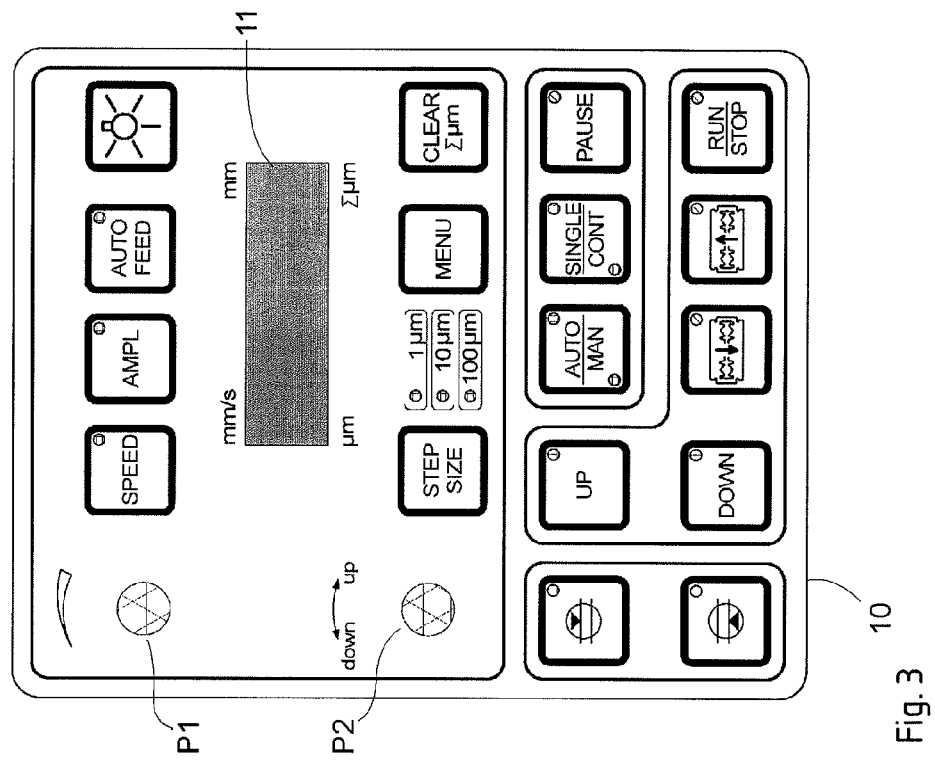
FIG. 3 shows the control panel of the vibrating microtome.

A control panel 10 that is shown in FIG. 3 is embodied, for example, as a separate control console that is connected to the vibrating microtome via a connecting cable. By way of control panel 10, values such as the vibration amplitude, Z position, and (for the sample holder only) the advance in the X direction can be set, and the result of the vertical runout measurement can be presented on display 11 along with other numerical values as necessary. The functions of those components of the control panel that are essential for the invention is evident from the discussion that follows; operating components that are not discussed here serve purposes that are not of significance for the invention or are reserved for later expansion.

Electronic Control System

Figure 4:
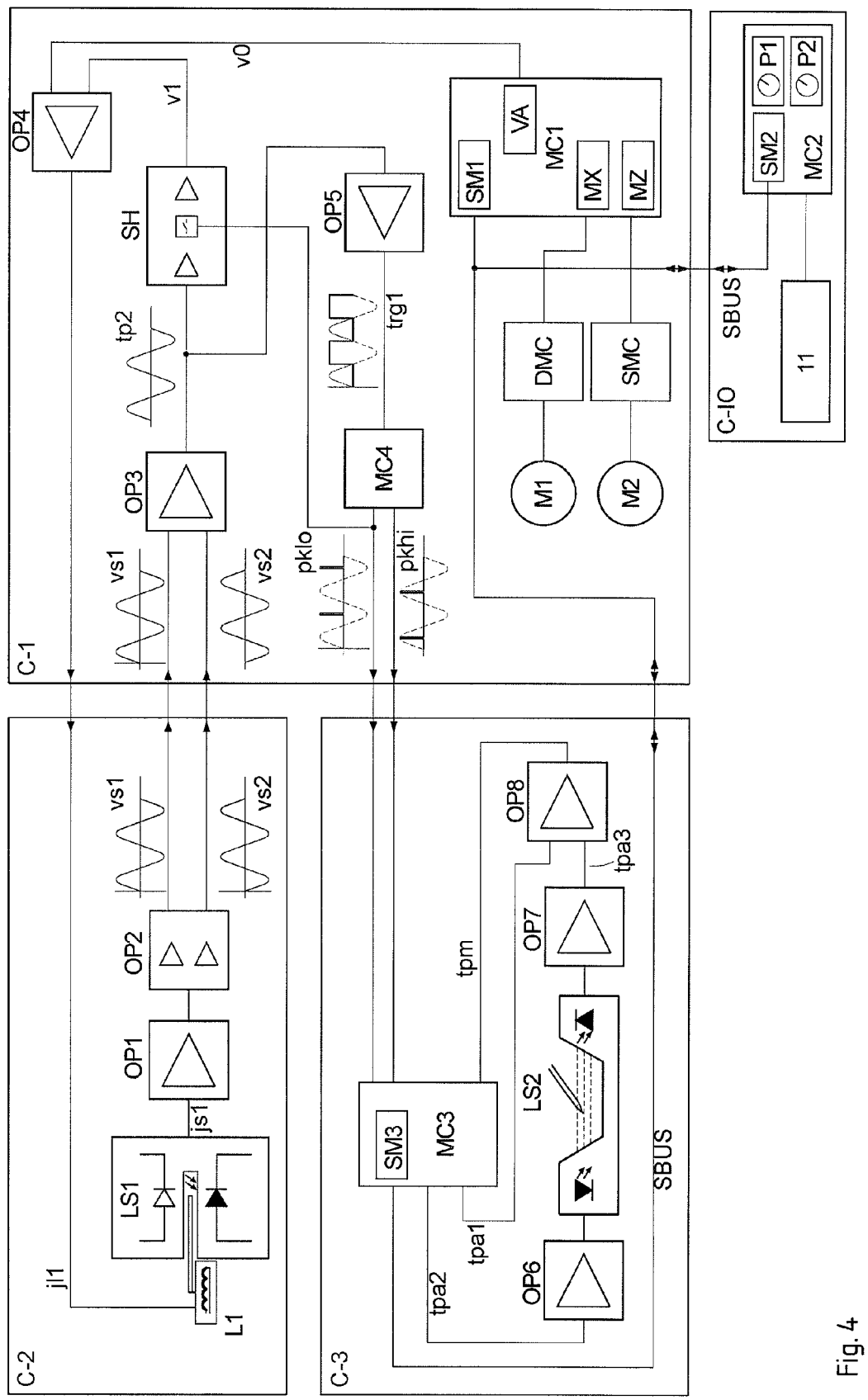
FIG. 4 is a block diagram showing the control system of the vibrating microtome and of the measuring head.

FIG. 4 is a block diagram of the control system of the vibrating microtome. The components of main control system C-1 are housed in the body of vibrating microtome 1; in addition, control and drive components are also present in vibrating head 2 (box C-2 in FIG. 4) and in the body of measuring head 3 (electronic measurement system C-3), and in control panel 10 (display system C-IO).

Vibrating head control system C-2 measures the amplitude deflection of vibrating head 2 and thus of knife holder 5. Drive is performed electromechanically using a stationary air-core coil L1 and permanent magnets (not shown; cf. in this regard the article by J. R. P. Geiger et al.) coupled to an aluminum base block. The base block, together with two laterally mounted leaf springs, forms a spring-mass system whose resonant frequency is determined by the spring constant and the mass of the drive head. The vibration profile is sinusoidal to high accuracy, so that the derived signals (unless otherwise indicated) are likewise sinusoidal. Drive current jl1 of air-core coil L1 is furnished by main control system C-1. The deflection of the system is measured by means of an IR light measurement section LS1 whose IR photodiode furnishes an alternating current corresponding to the vibration and having an overlaid DC component; this measured current js1 is amplified in a signal amplifier OP1 and converted into a voltage, the DC voltage component being separated out. This AC voltage signal is amplified again in a differential line output driver OP2, outputted as non-inverted and inverted voltage signals vs1, vs2, and conveyed to main control system C-1; the signal has, for example, a value of 1 V per mm of vibrating head deflection. The measured vibrating head motion signal is transferred in the form of two mutually inverted signals in order to compensate for interference occurring along the transfer path.

In main control system C-1, the two signals vs1, vs2 are converted by means of a differential amplifier OP3 (by calculating the difference of the two signals) into a control signal tp2 for the vibrating head vibration, e.g. in the form of an AC voltage signal. A sample-and-hold switch SH ascertains the amplitude width of control signal tp2 in the form of a DC voltage signal (e.g. 1 V per mm of vibration amplitude; signal range from 0 to 3000 mV). This signal is delivered as actual value v1 to an amplitude regulation circuit OP4 that compares it with setpoint v0 and, acting substantially as a PI controller, generates drive signal jl1 for drive coil L1 of the vibrating head at the operating vibration frequency.

From control signal tp2, a square-wave signal trg1 is derived by means of a zero-crossing detector OP5, and from the latter signal a maximum-minimum detector MC4 generates two control signals pklo, pkhi. Signals pklo, pkhi exhibit needle pulses at each point in time of the signal minimum and maximum of control signal tp2. One of the signals pklo, pkhi is delivered as a trigger signal to sample-and-hold switch SH discussed above. Both signals pklo, pkhi are delivered to electronic measurement system C-3 of the measuring head and act for the latter as control application signals (synchronization signals) for accurately timed definition of the vibration end points.

Electronic measurement system C-3 is located, for example, in the bottom of measuring head 3 and is controlled by a microcontroller MC3 that communicates with main control system C-1 and with display system C-IO, and comprises for that purpose a serial module SM3 that implements a serial bus SBUS in the manner of the known RS485. During the measurement operation, electronic measurement system C-3 is connected to main control system C-1, for example, via a cable conductor (not shown in FIGS. 1 and 2) that, in addition to serial bus SBUS and the signal conductors of signals pklo, pkhi, also contains the voltage supply (15 V) to the electronic measurement system.

The light barrier arrangement of the measuring head is represented symbolically in FIG. 4 by the reference character LS2. The transmitting diode is powered by a current supply OP6 that furnishes a supply current whose intensity is predetermined by microcontroller MC3 via a control signal tpa2. The detector diode furnishes a detector current that is converted by a signal amplifier OP7 into a voltage signal tpa3. In addition, a further amplifier OP8 can be provided that serves as an amplitude scaler in the manner of a multiplier, and maps the magnitude of voltage signal tpa3 onto a desired scale (e.g. 1 mV corresponding to 1 μm of knife travel, or 1 mV per rotation of setting screw 7); scale factor tpa1 is furnished to amplifier OP8 by microcontroller MC3. The (optionally scaled) voltage signal thereby obtained is delivered to microcontroller MC3 as a measured signal tpm.

Microcontroller MC3 determines the magnitude of measured signal tpm at each of the points in time defined by control application signals pklo, pkhi; the instantaneous values thereby obtained, which correspond to the positive and negative peak values of the oscillating signal tpm, are buffered in digitized form and a difference between the values is computed and sent via serial bus SBUS to display system C-IO. There the value is received by microcontroller MC2 and displayed as the transverse offset on display 11 of control panel 10. Alternatively, the two instantaneous peak values may be sent from microcontroller MC3 via serial bus SBUS to display system C-IO, and a difference between the values may be computed by control panel microcontroller MC2 and displayed as the transverse offset on display 11 of control panel 10.

Returning to main control system C-1, a microcontroller MC1 is in communication by means of a serial module SM1, via serial bus SBUS, with microcontrollers MC2, MC3 of control panel 10 and of measuring head 3. Microcontroller MC1 retains, for example in memory registers VA, MX, MZ, the values of the vibration amplitude (conveyed as setpoint signal v0 to controller OP4), sectioning feed speed, and section thickness, respectively. Using the values just recited, the motors, namely DC motor M1 for the X direction and stepping motor M2 for Z positioning, are controlled via respectively associated motor controllers DMC, SMC. The advance speed and the setpoint parameter for the Z position are set manually on the control panel, for example using control knobs P1, P2. Actuation of one of the buttons (FIG. 3) on the control panel is detected by control panel microcontroller MC2 in a manner known ser se, and is reported via serial bus SBUS (serial module SM2) to the main control system microcontroller MC1.

Vertical Runout Measurement

The procedure occurring in a vertical runout adjustment is, for example, as follows:

The electrical connection between measuring head 3 and the microtome is created, for example by plugging in the connecting cable (and, if applicable, by inputting a corresponding command on control panel 10). Readiness is indicated on control panel 10, for example by displaying "VCHECK" on display 11.

The user actuates the DOWN button on the control panel. The main control system causes the measuring head to be Z-positioned into the lowest position, and the vibrating head also moves the knife into the rearmost position. After installation of the knife 6 (and after any manual coarse setting of the knife inclination), clamping screw 12 is tightened. Measuring head 3 is installed on holder 4 and immobilized using clamping lever 4a.

Once installation is complete, the user actuates the RUN button. The main control system thereupon moves the vibrating head forward so that knife 6 is positioned above light barrier 9 of the measuring head. The light barrier is still completely exposed, and in the meantime measuring head microcontroller C-3 can usefully set the intensity of the light beam, via control signal tpa2, to a value at which output signal tpm is regulated to an output value that corresponds to 95% of the modulation capability of the detector element of the light barrier. Setting the intensity at the beginning of a vertical runout adjustment compensates for possible interfering influences such as extraneous light, temperature fluctuations, and so on.

The measuring head is then moved upward in the Z direction into a position in which the knife partly covers the light barrier. This is detected by the fact that because of the occlusion by the knife, signal tpm drops to a predetermined fraction of the initial value, for example 50%, with a tolerance of e.g. +/−1%. The measuring apparatus is thus at a working point at which the correlation between Z position and light quantity is linear, and that offers the greatest possible sensitivity.

If no occlusion can be achieved, a fault exists and the measuring head is moved back down into the lowest Z position.

Once positioning in the light barrier is achieved, vibration is started at the amplitude set on the control panel. The speed in the X direction is zero. Electronic measurement system C-3 now determines the vertical runout as described above with reference to FIG. 4, and sends the measurement result to microcontroller MC2 for display on the control panel. For example, a value "+3.4" might be displayed, which means that the vertical runout can be corrected with 3.4 clockwise rotations of the setting screw (a negative value would mean a counterclockwise rotation). The value displayed could also be scaled differently, for example in μm/mm (Z vertical runout as a function of offset in the X direction).

The user acknowledges the display, for example by actuating a specific button such as STOP or PAUSE. Vibration of the vibrating head is stopped, if it has not already been shut off once measurement is complete. The user can now adjust the knife inclination. For this, he or she loosens clamping screw 12, rotates setting screw 7 the amount indicated, and retightens clamping screw 12.

It should be noted that this adjustment operation is deliberately performed manually. Although it would be an additional simplification if, for example, a positioning motor or a piezoelement were provided for alignment of the knife inclination, experience has shown that—leaving aside the electrical and electronic complexity associated therewith—positioning elements of this kind would make the vibrating head unnecessarily heavy, which would unfavorably change the vibratory behavior of the vibrating head.

As a rule, the calibration is already sufficient after the first pass; it is nevertheless advisable to check the value by repeating the measurement operation and, if applicable, readjusting the knife inclination. For this, the user actuates the RUN button and the operation presented above proceeds from the beginning. In principle, the operation can be repeated as often as necessary, until the measurement yields a vertical runout of zero.

Because the associated Z position is set at each pass, any displacement of the Z position of the knife resulting from the adjustment is also simultaneously compensated for.

When adjustment is complete, the user actuates the DOWN button for confirmation. The measuring head is moved back into the lowest Z position and the knife is moved back. No buttons other than RUN (which starts a new measurement run as described above) are accepted. The system now waits for the measuring head to be removed and electrically disconnected from the microtome. A sample holder can now be installed and connected in its place; as soon as this has happened, a sectioning operation can begin, proceeding in the familiar manner on the basis of the parameters inputted via control panel 10, in particular vibration amplitude and Z position (by way of the UP and DOWN buttons).

Calibrating The Scale Factor

Calibration of the scale factor tpa1 is accomplished after input of a corresponding command on the control panel when measuring head 3 is connected, e.g. by actuating the AUTO/MAN button. The vibrating head is then brought into a position in which knife 6 is positioned above light barrier 9 of the measuring head. Measuring head microcontroller C-3 can, as described above, adjust the intensity of the light beam. The measuring head is then moved up in the Z direction into the position, described above, in which the knife partly covers the light barrier, and a measurement of the vertical runout is performed. The value of signal tpm is buffered by microcontroller MC3. The user is then requested, for example by output of an instruction via the display, to change the setting of adjusting screw 7 by exactly one clockwise rotation. When the user has executed this rotation and indicates so, for example by actuating the RUN button, a new measurement of the vertical runout is performed. From the difference between the two values of signal tpm, microcontroller MC3 determines the factor by which the present value of control signal tpa1 is to be corrected, performs the corresponding correction, and stores, in an EEPROM (not shown) provided by the microcontroller, the new value of signal tpa1 thus obtained.

What is claimed is:

1. A vibrating microtome and a measurement device, comprising:
   a knife adapted to vibrate in a direction parallel to a section plane and substantially parallel to a cutting edge of the knife;
   a light barrier oriented in a direction parallel to the section plane and the cutting edge partially covering a light beam of the light barrier;
   a measured signal (tpm) generated by the light barrier, wherein fluctuation of the measured signal (tpm) indicates the presence of a transverse offset of the cutting edge;
   at least one control application signal (pklo, pkhi) generated by a control application signal generator, the at least one control application signal (pklo, pkhi) describing a time course of the vibration of the knife; and
   a microcontroller for receiving the at least one control application signal (pklo, pkhi) and the measured signal (tpm), the microcontroller determining a magnitude of transverse offset based on the measured signal at points in time determined from the at least one control application signal (pklo, pkhi).

2. The vibrating microtome and measurement device of claim 1, wherein the at least one control application signal (pklo, pkhi) defines the points in time of the vibration maxima of the knife, and the microcontroller derives, from the measured signal (tpm), values that correspond to the transverse positions of the cutting edge at times of opposite vibration maxima, and determines the magnitude of transverse offset from a difference between the derived values.

3. The vibrating microtome and measurement device of claim 1, wherein the vibrating microtome comprises the knife and the microcontroller, and the measurement device comprises the light barrier and the control application signal generator; and
   wherein the measurement device is embodied as a unit detachable from the vibrating microtome with which it is used.

4. The vibrating microtome and measurement device of claim 1, further comprising a display for receiving the magnitude of transverse offset from the microcontroller and for displaying the magnitude of transverse offset.

5. A vibrating microtome system comprising:
   (i) a vibrating microtome including:
      a vibrating head;
      a knife having a cutting edge, the knife being arranged in the vibrating head to vibrate with the vibrating head in a direction parallel to a section plane and substantially parallel to the cutting edge; and
      an electronic control system (C-1) comprising:
         a vibration signal (tp2) generated by a vibration signal generator for driving vibration of the vibrating head;
         at least one control application signal (pklo, pkhi) generated by an application signal generator, the at least one control application signal (pklo, pkhi) describing a time course of the vibration of the knife from the vibration signal (tp2);
   (ii) a light barrier comprising a light beam oriented in a direction parallel to the section plane and partially covered by the cutting edge and for generating a measured signal (tpm) representing a fluctuation over time occurring because of a transverse offset of the cutting edge during vibration of the knife as a consequence of a potentially present inclination of the cutting edge with respect to the section plane; and
   (iii) an electronic measurement system (C-3) comprising:
      a microcontroller for receiving the at least one control application signal (pklo, pkhi) and for determining a magnitude of transverse offset of the cutting edge based on values of the measured signal (tpm) at points in time determined from the at least one control application signal (pklo, pkhi).

6. The vibrating microtome system according to claim 5, further comprising a display associated with the electronic control system, wherein the electronic measurement system further generates a signal that describes the magnitude of transverse offset, and the electronic control system accepts the signal that describes the magnitude of the measured transverse offset and displays the signal on the display.

7. The vibrating microtome system according to claim 5, wherein the at least one control application signal (pklo, pkhi) defines the points in time of the vibration maxima of the knife.

8. The vibrating microtome system according to claim 5, wherein the light barrier and the electronic measurement system are provided as a unit detachable from the vibrating microtome system.

* * * * *